(12) United States Patent
Immink et al.

(10) Patent No.: US 9,429,571 B2
(45) Date of Patent: Aug. 30, 2016

(54) SENSING DEVICE FOR SENSING A FLUID

(71) Applicant: KONINKLIJKE PHILIPS N.V., Eindhoven (NL)

(72) Inventors: Albert Hendrik Jan Immink, Eindhoven (NL); Jozef Franciscus Elisabeth Gootzen, Geldrop (NL); Dirk Jan Nelly Vananderoye, Bree (BE); Petrus Johannes Wilhelmus Van Lankvelt, Boekel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 201 days.

(21) Appl. No.: 14/452,082

(22) Filed: Aug. 5, 2014

(65) Prior Publication Data

US 2014/0342942 A1    Nov. 20, 2014

Related U.S. Application Data

(62) Division of application No. 13/140,175, filed as application No. PCT/IB2009/055540 on Dec. 7, 2009, now Pat. No. 9,040,285.

(30) Foreign Application Priority Data

Dec. 18, 2008    (EP) .................... 08172132

(51) Int. Cl.
| | |
|---|---|
| *G01N 33/558* | (2006.01) |
| *G01N 33/543* | (2006.01) |
| *G01N 21/03* | (2006.01) |
| *G01N 21/11* | (2006.01) |
| *G01N 21/552* | (2014.01) |

(52) U.S. Cl.
CPC ........ *G01N 33/54373* (2013.01); *G01N 21/03* (2013.01); *G01N 21/11* (2013.01); *G01N 21/552* (2013.01); *B01L 2200/027* (2013.01); *B01L 2200/04* (2013.01); *B01L 2300/048* (2013.01); *B01L 2300/0627* (2013.01); *B01L 2300/087* (2013.01); *B01L 2300/0816* (2013.01); *B01L 2300/14* (2013.01); *B01L 2400/0481* (2013.01); *G01N 2021/0346* (2013.01)

(58) Field of Classification Search
None
See application file for complete search history.

(56) References Cited

U.S. PATENT DOCUMENTS

| | | |
|---|---|---|
| 4,426,451 A | 1/1984 | Columbus |
| 4,849,340 A | 7/1989 | Oberhardt |
| 5,230,866 A | 7/1993 | Shartle |
| 5,300,779 A | 4/1994 | Hillman |
| 5,602,040 A | 2/1997 | May et al. |
| 2004/0121449 A1 | 6/2004 | Pugia |
| 2004/0231736 A1 | 11/2004 | Kim |
| 2005/0153430 A1 | 7/2005 | Ohtaka |

FOREIGN PATENT DOCUMENTS

| | | |
|---|---|---|
| EP | 0305210 A2 | 3/1989 |
| WO | 2006105110 A2 | 10/2006 |

*Primary Examiner* — Chris L Chin

(57) ABSTRACT

The invention relates to a sensing device for sensing a fluid. The sensing device comprises an inlet port (20) for receiving the fluid (100) and a measurement chamber (25) for sensing the fluid (100). The sensing device further comprises a fluid channel (30) coupling the inlet port (20) and the measurement chamber (25) for transporting the fluid (100) from the inlet port (20) to the measurement chamber (25) and a fluid stop unit (50) for stopping and controllably releasing the flow of fluid between the inlet port (20) and the measurement chamber (25). This allows stopping the fluid before reaching the measurement chamber (25) and controllably releasing the fluid for allowing the fluid to flow into the measurement chamber (25), if the sensing device is ready for analyzing the fluid.

5 Claims, 8 Drawing Sheets

SENSING DEVICE FOR SENSING A FLUID

CROSS REFERENCE TO RELATED APPLICATIONS

This application is a divisional of U.S. application Ser. No. 13/140,175 filed Jun. 16, 2011, which is a national filing of international application serial no. PCT/IB2009/055540, filed Dec. 8, 2011, which claims the benefit of EP application serial no. 08172132.6, filed Dec. 18, 2008, all of which are incorporated herein by reference.

FIELD OF THE INVENTION

The present invention relates to a sensing device and method for sensing a fluid and an analyzing apparatus for analyzing a fluid.

BACKGROUND OF THE INVENTION

Sensing devices like sensing cartridges can be part of bio sensors or chemical sensors. Such sensing cartridges typically comprise an inlet port and a measurement chamber, which are connected via a fluid channel. In the measurement chamber a sensor surface is provided which can interact with particles of the fluid applied into the inlet port and transported through the fluid channel. The fluid channels are typically capillary fluid channels such that a fluid introduced into the inlet port autonomously travels through the fluid channel to the measurement chamber. This can take between 10 and 60 seconds. It is, however, important to have reproducible results. The results may, however, differ depending on the time elapsed between applying the fluid to the inlet port and the measurement of the fluid in the measurement chamber. This problem can be avoided by inserting the cartridge directly into an analyzer after the fluid has been applied to the inlet port which may not always be possible. On the other hand, if the cartridge is inserted into the analyzer before the fluid is applied into the inlet port, a danger of contamination of the analyzer may be present.

SUMMARY OF THE INVENTION

It is an object of the invention to provide a sensing device and a sensing method for sensing a fluid, wherein the reproducibility of the results can be increased, in particular, without contaminating an analyzing apparatus, if the sensing device is used together with the analyzing apparatus for analyzing the fluid. It is a further object of the present invention to provide a corresponding analyzing apparatus, which can be used together with the sensing device for analyzing the fluid.

In an aspect of the present invention a sensing device for sensing a fluid is presented, which comprises:
  an inlet port for receiving the fluid;
  a measurement chamber for sensing the fluid;
  a fluid channel coupling the inlet port and the measurement chamber for transporting fluid from the inlet port to the measurement chamber; and
  a fluid stop unit for stopping and controllably releasing the flow of fluid between the inlet port and the measurement chamber.

With such a sensing device a droplet of fluid can be applied into the inlet port, wherein the fluid flows partly along the fluid channel but not into the measurement chamber. As long as the fluid is in the fluid channel it is protected from contamination and also the fluid can not contaminate an analyzing apparatus which might be used together with the sensing device for analyzing the fluid. Once the fluid is released again it can continue to flow into the measurement chamber.

Since this releasing is performed controllably, the flow of the fluid into the measurement chamber can be controlled such that the fluid flows in the measurement chamber if the sensing device is ready for sensing the fluid or, if the sensing device is used in combination with an analyzing apparatus, if the sensing device has been inserted into the sensing device and if the analyzing apparatus is ready for analyzing the fluid. These effects of the sensing device allow increasing the reproducibility of the results of sensing or analyzing the fluid, in particular, without contaminating an analyzing apparatus, which might be used for analyzing the fluid present in the measurement chamber of the sensing device.

The sensing device itself can be adapted to sense the fluid or the sensing device can be adapted to cooperate with a further device like an analyzing apparatus for sensing the fluid.

Sensing or analyzing the fluid includes, for example, detecting target elements in the fluid, wherein the amount or concentration of target elements in the fluid can be regarded as a property of the fluid.

The sensing device can comprise several inlet ports and/or several measurement chambers and/or several fluid channels and/or several fluidic stop units.

Preferably, the fluid stop unit comprises a venting hole arranged behind the measurement chamber with respect to a flow direction from the inlet port to the measurement chamber and coupled to the fluid channel as well as a seal arranged at the venting hole for hermetically sealing the venting hole. The stop of the fluid in the fluid channel can be released by puncturing the seal arranged at the venting hole. Such a puncturing will release air which was previously enclosed in the venting hole and the fluid channel.

The seal is preferentially a foil like an aluminum foil or a plastic foil or a membrane which can be injection molded. If the seal is implemented as a foil or a membrane, the seal can be easily punctured in order to release the enclosed air or gas in the fluid channel and in the venting hole.

Preferentially, the fluid channel is a capillary fluid channel such that the fluid introduced into the fluid channel can travel along the fluid channel independently only driven by capillary forces.

Preferentially, a filter unit can be arranged between the inlet port and the measurement chamber for filtering the fluid in order to remove particles in the fluid. By means of this filter unit unwanted particles in the fluid can be removed.

It is preferred that the fluid stop comprises a fluidic stop element arranged along the fluid channel for stopping a flow of fluid between the input port and the measurement chamber. The fluid stop unit furthermore comprises a pressure control unit for controlling a pressure in a first part of the fluid channel between the inlet port and the fluidic stop element by changing the pressure in the first part of the fluid channel to force the fluid past the at least one fluidic stop element. The flow of the fluid in the fluid channel can be stopped by means of a fluidic stop element and can be released again by changing the pressure in a first part of the fluid channel such that the fluid is forced past the fluidic stop element. Accordingly, a controllable stop of the flow of the fluid can be achieved.

The sensing device can comprise several pressure control units.

It is preferred that the pressure control unit comprises a cap arranged a first section of the sensing device comprising the inlet port, the cap having an opened position and a closed position. In the opened position the inlet port is uncovered by the cap and a first pressure is present in the first part of the fluid channel. In the closed position the inlet port is sealed, in particular, hermetically sealed, by the cap and a second pressure is produced in the first part of the fluid channel. The second pressure is higher than the first pressure to force the fluid in the fluid channel past the fluidic stop element into the measurement chamber. Preferentially, the cap is slidable for moving the cap from the opened to the closed position. The provision of the cap constitutes an easy and convenient way to overcome the fluidic stop element and release the flow of the fluid again. As the cap covers the inlet port in its closed position, a contamination of the fluid in the inlet port or in the first part of the fluid channel is avoided.

It is further preferred that the sensing device comprises a sealing unit for sealing the cap and the first section of the device, at least if the cap is in the closed position. The sealing unit facilitates the provision of the second increased pressure in the first part of the fluid channel.

It is further preferred that the cap is irreversibly locked in the closed position. Hence, a manipulation of the fluid in the fluid channel can be avoided. Moreover, a multiple use of the same sensing device is prevented. It is further preferred that the pressure control unit comprises a first hole coupled to the first part of the fluid channel for introducing a pressure into the first part of the fluid channel to force the fluid past the fluidic stop unit. By means of the first hole, for example, air can be pressed into the fluid channel to force the fluid past the fluidic stop element.

It is further preferred that the pressure control unit comprises an air chamber coupled to the first part of the fluid channel. The air chamber comprises an elastic cover, which might be a membrane or a foil, for covering, in particular, sealing, an opening of the air chamber. Accordingly, merely by pressing the elastic cover, the pressure in the first part of the fluid channel can be increased to force the fluid past fluidic stop element.

The sensing device can comprise several air chambers.

It is further preferred that the sensing device is adapted to be cooperable with an analyzing apparatus for allowing the analyzing apparatus to sense the fluid in the measurement chamber. This allows using several sensing devices with the same analyzing apparatus. In particular, the sensing device can be a sensing cartridge, which can be disposed after being used.

In a further aspect of the present invention an analyzing apparatus for analyzing a fluid is provided. The analyzing apparatus is adapted to be cooperable with a sensing device which comprises an inlet port for receiving a fluid, a measurement chamber for sensing the fluid, a fluid channel coupling the inlet port and the measurement chamber for transporting fluid from the inlet port to the measurement chamber, and a fluid stop unit for stopping and controllably releasing the flow of fluid between the inlet port and the measurement chamber. The analyzing apparatus comprises a sensing device receiving unit for receiving the sensing device. The analyzing apparatus further comprises a fluid releasing unit for controllably releasing a flow of fluid stopped between the inlet port and the measurement chamber of the sensing device, if the sensing device is inserted into the sensing device receiving unit.

The analyzing apparatus can comprise several fluid releasing units.

It is preferred that the fluid releasing unit comprises a puncture element for puncturing a seal covering a venting hole arranged behind the measurement chamber with respect to a flow direction from the inlet port to the measurement chamber, when the sensing device is inserted into the sensing device receiving unit. By means of the puncture element, the seal can be punctured to release any gas or air trapped in the fluid channel and the venting hole.

It is further preferred that the fluid releasing unit comprises a pressure generating unit for generating a fluid pressure and a second hole coupled to the pressure generating unit for pressing pressure fluid like air or like another gas into a first hole of an inlet port of a sensing device inserted into the sensing device receiving unit for increasing the pressure in the fluid channel such that the flow of fluid between the inlet port and the measurement chamber is controllably released.

The analyzing apparatus can comprise several pressure generating units coupled to several second holes for pressing a pressure fluid into several first holes and/or several inlet ports of a sensing device.

It is further preferred that the fluid releasing unit comprises an actuator unit for pressing against an elastic cover of a sensing device inserted into the sensing device receiving unit for increasing the pressure in the fluid channel such that the flow of fluid between the inlet port and the measurement chamber is controllably released. By means of the actuator, the pressure inside an air chamber in the sensing device can be increased to force the fluid past the fluidic stop.

It is further preferred that the sensing device comprises an inlet cover and optionally also a sealing element like a sealing ring arranged around the inlet port, wherein the inlet cover is adapted to be moveable between a closed position and an open position and wherein in the closed position the inlet port is closed and in the open position the inlet port is open. This allows preventing that the fluid leaves the fluid channel via the inlet port, in particular, if the pressure is increased within the fluid channel for releasing the stop of flow between the inlet port and the measurement chamber.

In a further aspect of the invention a method for sensing a fluid is presented. A sensing device having an inlet port for receiving the fluid, a measurement chamber for sensing the fluid, a fluid channel coupling the inlet port and the measurement chamber for transporting fluid from the inlet port to the measurement chamber and a fluid stop unit for stopping and controllably releasing the flow of fluid between the inlet port and the measurement chamber is provided. The fluid is received at the inlet port. The fluid from the inlet port is transported to the measurement chamber. The flow of fluid is stopped and controllably released between the inlet port and the measurement chamber.

It is preferred that at least one droplet of fluid is inserted into an inlet port of the sensing device. Then, the sensing device is inserted into a sensing device receiving unit of an analyzing apparatus. The flow of fluid is stopped and controllably released between the inlet port and the measurement chamber.

Preferentially, a seal covering a venting hole of the sensing device is punctured when the second end of the sensing device is inserted into the sensing device receiving unit for controllably releasing the flow of fluid between the inlet port and the measurement chamber.

It is further preferred that air is pressed into a first hole or an inlet port of the sensing device when the sensing device is inserted into the sensing device receiving unit to force the fluid stopped by the fluidic stop element past the fluidic stop element into a measurement chamber of the sensing device.

It shall be understood that the sensing device, the analyzing apparatus and/or the method for sensing a fluid described have similar and/or identical preferred embodiments as described herein and/or defined in the dependent claims.

It shall be understood that a preferred embodiment of the invention can also be any combination of the dependent claims with the respective independent claims.

BRIEF DESCRIPTION OF THE DRAWINGS

These and other aspects of the invention will be apparent from and elucidated with reference to the embodiments described herein after. In the following drawings.

DETAILED DESCRIPTION OF EMBODIMENTS

Figure 1:
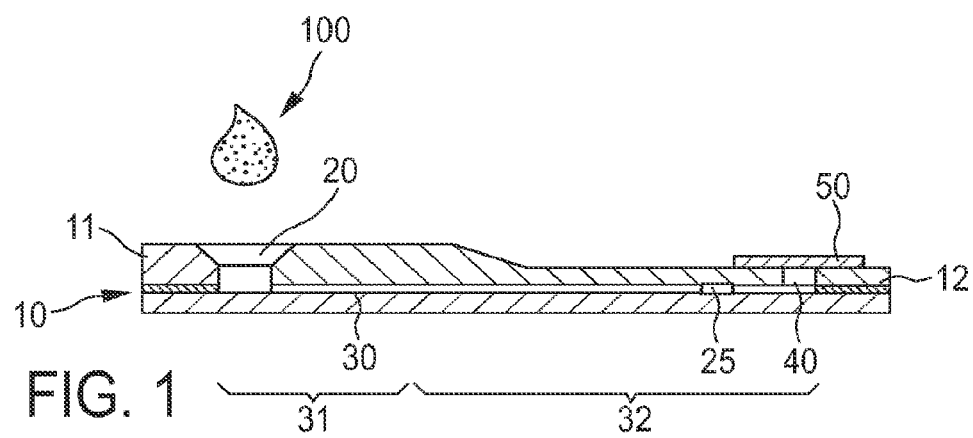
FIG. 1 shows schematically and exemplarily a sectional view of a sensing device.

FIG. 1 shows schematically and exemplarily a sectional view of a sensing device being a sensing cartridge according to a first embodiment. The sensing cartridge 10 comprises first and second ends 11, 12. At the first end 11 an inlet port 20 is provided and at the second end 12 at least one venting hole 40 and at least one measurement chamber 25 is provided. The venting hole 40 is sealed by a seal 50. Furthermore, a fluid channel 30 having first and second parts 31, 32 couples the inlet port 20, the measurement chamber 25 and the venting hole 40. In the first part 31 the fluid is stopped, before it is controllably released into the second part 32 for flowing into the measurement chamber 25.

The inlet port 20 serves to receive at least one droplet of a fluid 100, wherein the properties of the fluid 100 are to be measured or determined. The seal 50 preferably hermetically seals the venting hole 40. Preferably, the seal 50 is applied to the venting hole 40 during the manufacturing of the sensing cartridge.

Figure 2:
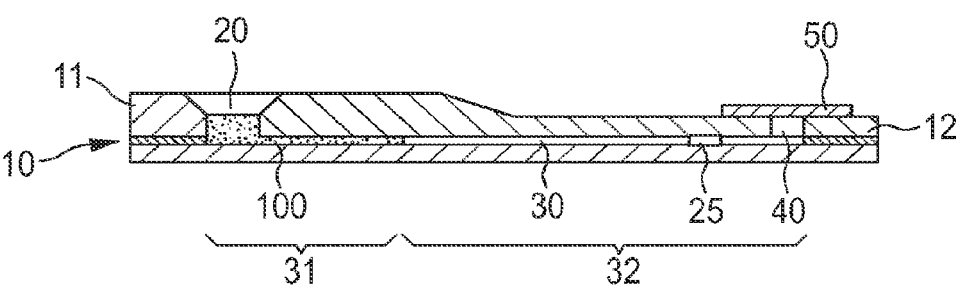
FIG. 2 shows schematically and exemplarily a further sectional view of the sensing device.

FIG. 2 shows schematically and exemplarily a further sectional view of the sensing cartridge of FIG. 1. In FIG. 2 a droplet of fluid 100 has been introduced into the inlet port 20 and the fluid 100 has travelled along the first part 31 of the fluid channel 30. Preferably, the fluid channel 30 is a capillary fluid channel, i.e. the fluid 100 travels along the fluid channel 30 by means of capillary forces. As the venting hole 40 is hermetically sealed by the seal 50, the fluid 100 can only travel a first distance of the first part 31 along the fluid channel 30. The fluid 100 will stop at a position where the force generated by the pressure in the remaining unfilled fluid channel 30 is at least equal to the capillary forces in the fluid channel 30. Accordingly, in FIG. 2 the situation is disclosed where the droplet of the fluid 100 has been introduced into the inlet port and the fluid has partly travelled along the fluid channel 30, i.e. along the first part 31 of the fluid channel 30, but the fluid has not yet reached the measurement chamber 25. In the situation as depicted in FIG. 2 flow of the fluid in the fluid channel 30 has been stopped.

Figure 3:
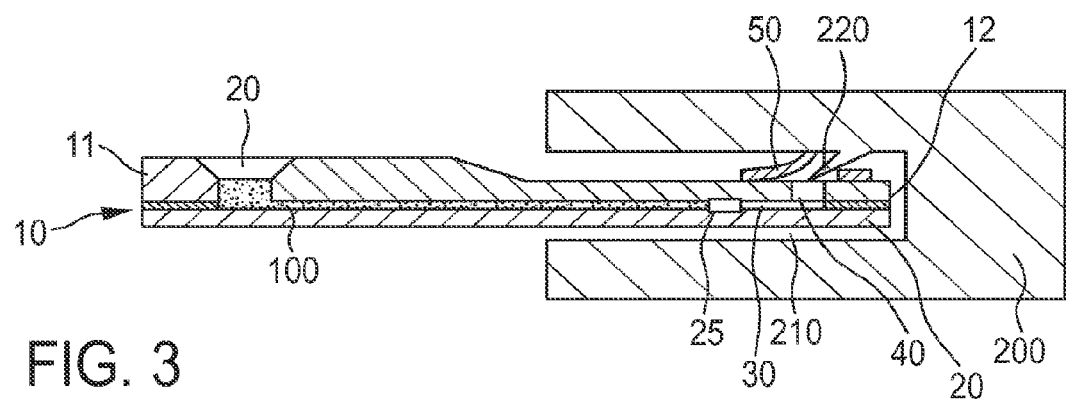
FIG. 3 shows schematically and exemplarily a further sectional view of the sensing device inserted into an analyzing apparatus.

FIG. 3 shows schematically and exemplarily a sectional view of the sensing cartridge inserted into an analyzing apparatus 200 which is also only schematically shown. Here, the second end 12 of the sensing cartridge 10 (as described according to FIGS. 1 and 2) is inserted into a sensing device receiving unit 210 of the analyzing apparatus 200. In the sensing device receiving unit 210 a puncture element 220 like a needle is provided such that it punctures the seal 50 covering the venting hole 40 when the second end 12 of the sensing cartridge 10 is inserted into the sensing device receiving unit 210. By puncturing the seal 50 the gas enclosed in the second part of the fluid channel 30 and in the venting hole 40 can be released such that the fluid 100 in the fluid channel 30 can travel along the second part 32 of the fluid channel 30 towards the measurement chamber 25. When the fluid has reached the measurement chamber 25, the fluid can be analyzed, i.e. e.g. properties of the fluid can be determined, by the analyzing apparatus. For example, the concentration of target elements in the fluid present in the measurement chamber can be determined as a property of the fluid for analyzing the fluid.

The seal 50 can be implemented as a foil which might be an aluminum foil and which is glued over the venting hole 40. Alternatively, the seal 50 can be implemented as a membrane which is injection molded.

It should be noted that when the seal is punched by the puncture element 50 the flow of the fluid inside the fluid channel can still be determined by capillary forces and is thus independent of any operator.

In addition, optionally a filter unit can be provided along the fluid channel 30 for filtering the fluid in order to remove particles in the fluid, for example red blood cells, if the fluid is blood.

Figure 4:
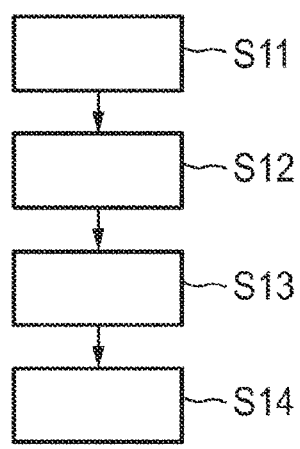
FIG. 4 shows a flow chart illustrating exemplarily a method for sensing a fluid in a sensing device.

FIG. 4 shows a flow chart illustrating exemplarily a method for sensing a fluid, i.e. in this embodiment for determining a property of a fluid in a sensing cartridge. In step S11, a droplet of fluid 100 is inserted into the inlet port 30. In step S12, the sensing cartridge 10 is inserted into the sensing device receiving unit 210 and in step S13 the seal is punctured such that the fluid 100 will continue to flow into the measurement chamber 25. In step S14, a measurement is performed when the fluid 100 has reached the measurement chamber 25.

Figure 5:
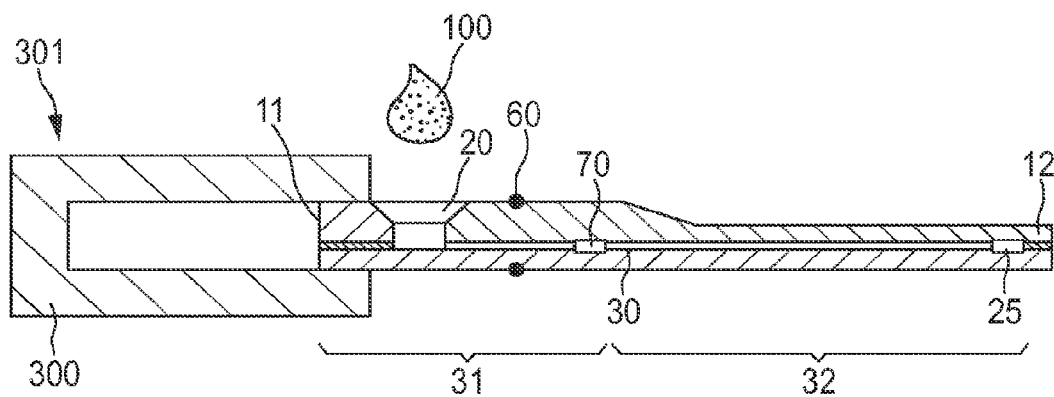
FIG. 5 shows schematically and exemplarily a sectional view of a further sensing device.

FIG. 5 shows schematically and exemplarily a sectional view of a further embodiment of a sensing device being a sensing cartridge. The sensing cartridge 10 comprises first and second ends 11, 12. An inlet port 20 for receiving a droplet of fluid 100 is arranged at the first end 11 and a measurement chamber 25 is arranged at the second end 12. Furthermore, a fluid channel 30 having first and second parts 31, 32 couples the inlet port 20 and the measurement chamber 25. Along the fluid channel 30 a fluidic stop unit 70 is provided. Optionally a sealing unit 60 can be provided between the inlet port 20 and the second end 12, further preferred between the inlet port 20 and the fluidic stop unit 70. The sealing unit 60 is, in this embodiment, a sealing ring. The sensing cartridge 10 further comprises a cap 300 which preferably has substantially a U-shape in cross-section. However, it should be noted that also other shapes are possible as long as the shape of the cap 300 corresponds to the shape of the first end 11 of the sensing cartridge. The cap 300 is shown in a first or opened position 301 leaving the inlet port 20 uncovered to allow an insertion of fluid. The cap 300 has been designed to at least partly hermetically fit over the first end 11 of the sensing cartridge 10 and to at least partly hermetically seal the inlet port 20 when in the closed position 302.

Figure 6:
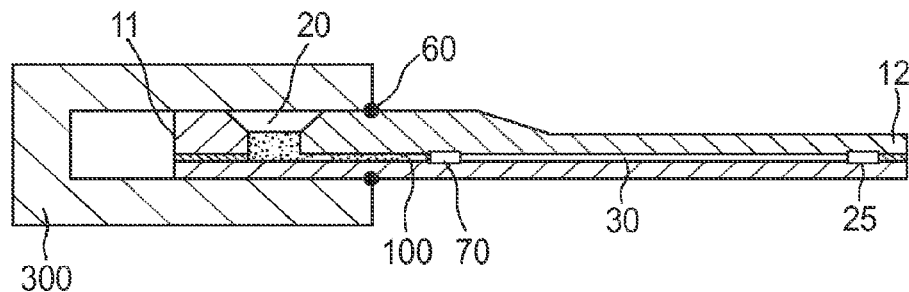
FIG. 6 shows schematically and exemplarily a further sectional view of the sensing device.

FIG. 6 shows schematically and exemplarily a further sectional view of the sensing cartridge. In FIG. 6 the situation is disclosed where a droplet of fluid 100 has been introduced into the inlet port 20 and the fluid 100 has traveled along the first part 31 of the fluid channel 30 until it reaches the fluidic stop unit 70. Moreover, the cap 300 has been partly placed over the second end 11 of the sensing cartridge and has reached the sealing ring 60. The fluid 100 in the fluid channel 30 will not travel further than the fluidic stop unit 70 as the driving capillary forces will not be high enough to force the fluid 100 past the fluidic stop unit 70. The fluidic stop unit 70 can be a geometrical feature and/or a local hydrophobisation while the fluid channel 30 is hydrophilic.

Figure 7:
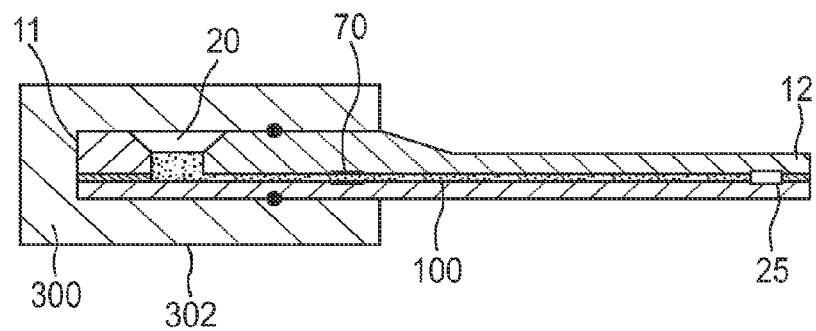
FIG. 7 shows schematically and exemplarily a further sectional view of the sensing device.

FIG. 7 shows schematically and exemplarily a further sectional view of the sensing cartridge. In FIG. 7 the cap 300 has been completely provided over the first end 11 of the sensing cartridge 10, i.e. it is in a second or closed position. Now, the ends of the cap 300 have been pushed over the sealing unit 60 such that the air pressure in the inlet port 20 increases to an extend that the fluid 100 in the fluid channel 30 is forced past the fluidic stop unit 70 along the second part 32 and can reach the measurement chamber 25. The air or another gas present in the space surrounded by the cap 300 is forced into the fluid channel 30 while moving the cap 300 from the opened position to the closed position. In order to allow the gas to be transferred from the space surrounded by the cap 300 to the fluidic channel 30, the part of the surface of the sensing device at which the inlet port is provided may comprises a recessed channel (not shown in FIGS. 5 to 7) for guiding the gas from the space surrounded by the cap 300 via the recessed channel and via the inlet port 20 into the fluid channel 30. In another embodiment, another gas connection might be present in the sensing cartridge for guiding the gas surrounded by the cap 300 into the fluid channel 30.

Accordingly, in FIG. 7 the situation is disclosed where the inlet port 20 is completely covered by the cap 300 and the fluid 100 has reached the measurement chamber 25 such that a measurement of properties of the fluid can start.

Preferably, the cap 300 will latch or click into its end position 302. Preferably the latching or the click is irreversible such that the cartridge can be removed in a sealed state from the analyzing apparatus. This is advantageous as a contamination of the analyzing apparatus can be avoided.

Preferably, the fluid channel 30 can be designed such that the fluid which has passed the fluidic stop 70 can continue to flow by capillary action along the second part 32.

If the fluidic stop unit 70 is embodied as a hydrophobic area or region, the fluid channel 30 is designed to avoid that the stream of the fluid breaks up after the hydrophobic region when the external pressure has been applied.

Figure 8:
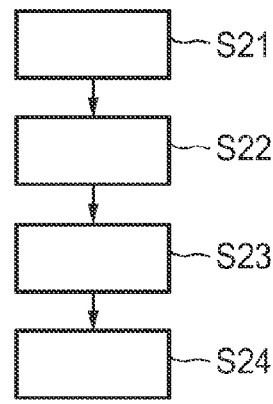
FIG. 8 shows a flow chart illustrating exemplarily a method for sensing a fluid in a sensing device according to a further embodiment.

FIG. 8 shows a flow chart illustrating exemplarily a method for analyzing a fluid in a sensing cartridge according to a further embodiment. In step S21, a droplet of fluid 100 is inserted into the inlet port 20. In step S22, the cap 300 slides from the open to the closed position forcing the fluid 100 past the fluidic stop element 70 into the measurement chamber 25. In step S23, the sensing cartridge 10 is inserted into the sensing device receiving unit 210. In step S24 a measurement is performed when the fluid 100 has reached the measurement chamber 25. In another embodiment, step S23 can be performed before step S22.

Figure 9:
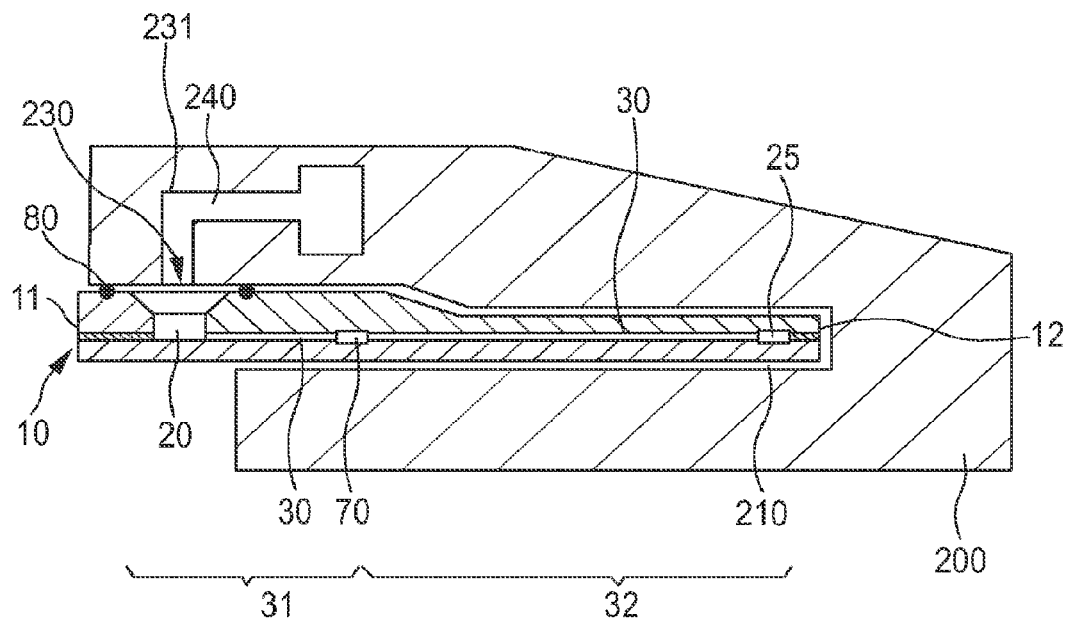
FIG. 9 shows schematically and exemplarily a sectional view of a sensing device and an analyzing apparatus according to a further embodiment.

FIG. 9 shows schematically and exemplarily a sectional view of a sensing cartridge inserted into an analyzing apparatus according to a further embodiment. The sensing cartridge 10 comprises first and second ends 11, 12, an inlet port 20, a fluid channel 30 having first and second parts 31, 32, a fluidic stop element 70 and a measurement chamber 25. The fluid channel 30 connects the input port 20, the fluidic stop element 70 and the measurement chamber 25. The sensing cartridge substantially corresponds to the sensing cartridge described above with reference to FIGS. 5 to 7, without the cap 300 and the sealing ring 60. The sensing cartridge according to the present embodiment comprises a sealing 80 arranged around the inlet port 20.

The analyzing apparatus 200 comprises a sensing device receiving unit 210 with a hole 230 and an air pressure generating unit 240 coupled to the hole 230 via a coupling channel 231 such that air pressure generated by the air pressure generating unit 240 can be transferred to the hole 230. When the sensing cartridge 10 is inserted into the sensing device receiving unit 210 the hole 230 in the analyzing apparatus is aligned with the inlet port 20. Then, the air pressure in the inlet port 20 is increased by means of the hole 230 such that fluid in the first part 31 of the fluid channel 30 is forced past the fluidic stop unit 70 along the second part 32 of the fluid channel 30. The increase of the air pressure in the hole 230 is determined or controlled by the air pressure generating unit 240.

Figure 10:
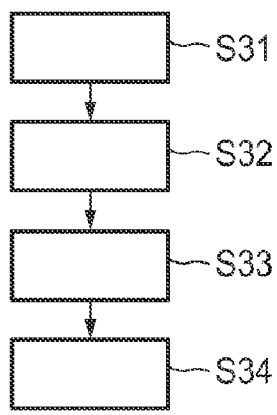
FIG. 10 shows a flow chart illustrating exemplarily a method for sensing a fluid in a sensing device.

FIG. 10 shows a flow chart illustrating exemplarily a method for analyzing a fluid in a sensing cartridge according to a further embodiment. In step S31 a droplet of fluid 100 is inserted into the inlet port 20 and in step S32 the sensing cartridge 10 is inserted into the sensing device receiving unit 210. In step S33 air is pressed into the inlet port forcing the fluid past the fluidic stop element 70 into the measurement chamber 25. In step S34 a measurement is performed when the fluid 100 has reached the measurement chamber 25. Step S31 is always performed before step S33. However, step S32 can also be performed before step S31.

Figure 11:
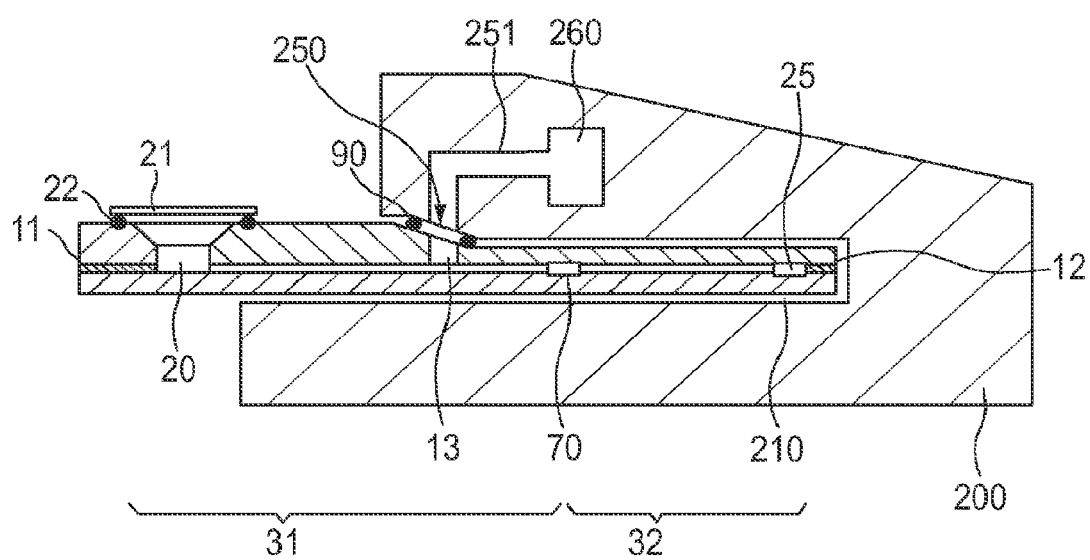
FIG. 11 shows schematically and exemplarily a sectional view of a sensing device and an analyzing apparatus according to a further embodiment.

FIG. 11 schematically and exemplarily shows a further sectional view of a sensing cartridge inserted into an analyzing apparatus according to a further embodiment. This sensing cartridge substantially corresponds to the sensing cartridge described above with reference to FIGS. 5 to 7, without the cap 300 and the sealing ring 60. In addition, the sensing cartridge comprises a hole 13 which couples the fluid channel 30 to the outside. Furthermore, a sealing ring 90 can be provided adjacent to the hole 13.

The analyzing apparatus 200 comprises a sensing device receiving unit 210 for receiving a second end 12 of the sensing cartridge 10. The analyzing apparatus 200 further comprises a hole 250 and an air pressure generating unit 260 coupled to the hole 250 via a coupling channel 251 such that air pressure can be generated at the hole 250 by the air pressure generating unit 260. When the second end 12 of the sensing cartridge 10 is inserted into the sensing device receiving unit 210, the hole 13 will be aligned with the hole 250. Then, the air pressure in the hole 13 can be increased by means of the air pressure generating unit 260. Hence, this increased air pressure will in turn increase the pressure in the fluid channel 30 and forces the fluid 100 past the fluidic stop unit 70 into the measurement chamber 25.

The sensing cartridge further comprises an inlet cover 21 for covering the inlet port 20 such that the fluid does not leave the sensing cartridge via the inlet port 20, if the pressure is increased in the fluid channel 30. The inlet cover 21 is, for example, a slidable element or a flap. The inlet cover 21 is moveable between a closed position, in which the inlet port 20 is closed, and an open position, in which the inlet port 20 is open for receiving the fluid. The inlet cover 21 further comprises a sealing element 22 like a sealing ring for reducing the probability that the fluid leaves the fluid channel 30 via the inlet port 20, if the pressure is increased within the fluid channel.

Figure 12:
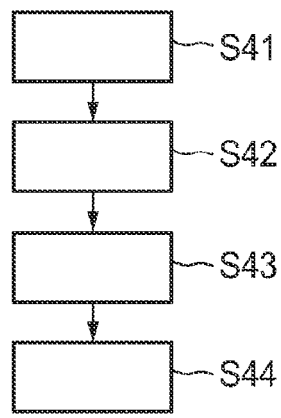
FIG. 12 shows a flow chart illustrating exemplarily a method for sensing a fluid in a sensing device according to a further embodiment.

FIG. 12 shows a flow chart illustrating exemplarily a method for sensing a fluid in a sensing cartridge according to a further embodiment. In step S41, a droplet of fluid 100 is inserted into the inlet port 30 and the inlet cover 21 is closed. In step S42 the sensing cartridge 10 is inserted into the sensing device receiving unit 210. In step 43, air is pressed into the hole 13 by means of the hole 250 in the analyzing apparatus forcing the fluid past the fluidic stop element 70 into the measurement chamber 25. In step S44 a measurement is performed when the fluid 100 has reached the measurement chamber 25. Also here, step S41 can be performed after step S42 has been performed.

Instead of using the inlet cover 21 the analyzing apparatus can be adapted to close the inlet port 20 of the sensing cartridge, if the sensing cartridge has been received in the sensing device receiving unit.

Figure 13:
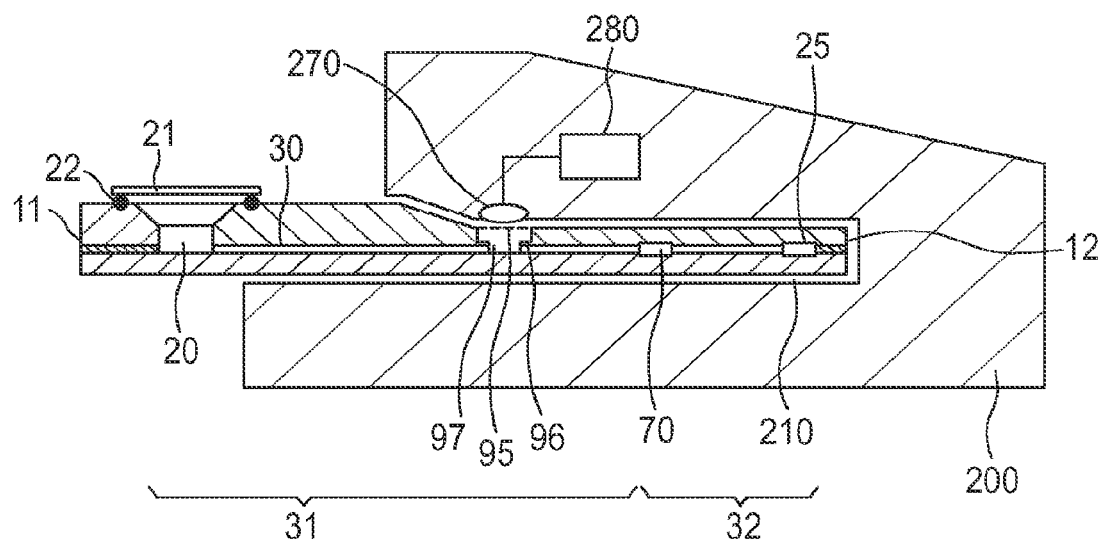
FIG. 13 shows schematically and exemplarily a sectional view of a sensing device and an analyzing apparatus according to a further embodiment.

FIG. 13 shows schematically and exemplarily a sectional view of a sensing device being a sensing cartridge and an analyzing apparatus according to a further embodiment. The sensing cartridge comprises first and second ends 11, 12, an inlet port 20, a fluid channel 30, a fluidic stop unit 70 and a measurement chamber 25. The sensing cartridge 10 further comprises an air chamber 96 which is coupled with the fluid channel 30 via a hole 97. The air chamber 96 is closed by means of an elastic membrane 95.

The analyzing apparatus 200 comprises a sensing device receiving unit 210, an actuator unit 270 and optionally an actuator control unit 280. When the second end 12 of the sensing cartridge 10 is inserted into the sensing device receiving unit 210, the air chamber 96 and the membrane 95 are aligned with the actuator unit 270. The actuator control unit 280 can control the actuator 270 to mechanically press against the membrane 95 such that the pressure in the air chamber 96 and the hole 97 is increased. This increased air pressure will force the fluid 100 in the fluid channel 30 past the fluidic stop unit 260 and into the measuring chamber 25. The sensing cartridge and the analyzing apparatus are advantageous as the amount of pressure which is applied to the air chamber can be controlled very accurately and reliable.

Also in this embodiment, the sensing cartridge comprises the inlet cover 21 and the sealing element 22.

Figure 14:
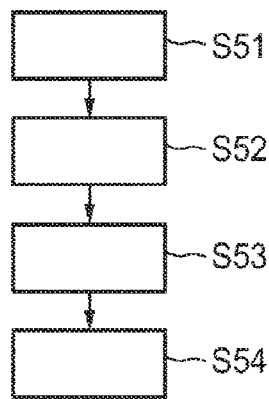
FIG. 14 shows a flow chart illustrating exemplarily a method for sensing a fluid in a sensing device according to a further embodiment.

FIG. 14 shows a schematic flow chart of a method for sensing a fluid in a sensing cartridge according to a further embodiment. In step S51, a droplet of fluid 100 is inserted into the inlet port 20 and the inlet port cover 21 is closed. In step S52 the sensing cartridge 10 is inserted into the sensing device receiving unit 210. In step S53, the elastic membrane 95 of the sensing cartridge is pressed down by means of an actuator unit 270 of the analyzing apparatus such that the air in the air chamber 96 is forced into the first part of the fluid channel 30 forcing the fluid past the fluidic stop element 70 into the measurement chamber 25. In step S54, a measurement is performed when the fluid 100 has reached the measurement chamber 25. Also in this embodiment step S51 can be performed after step S52 has been performed.

Figure 15:
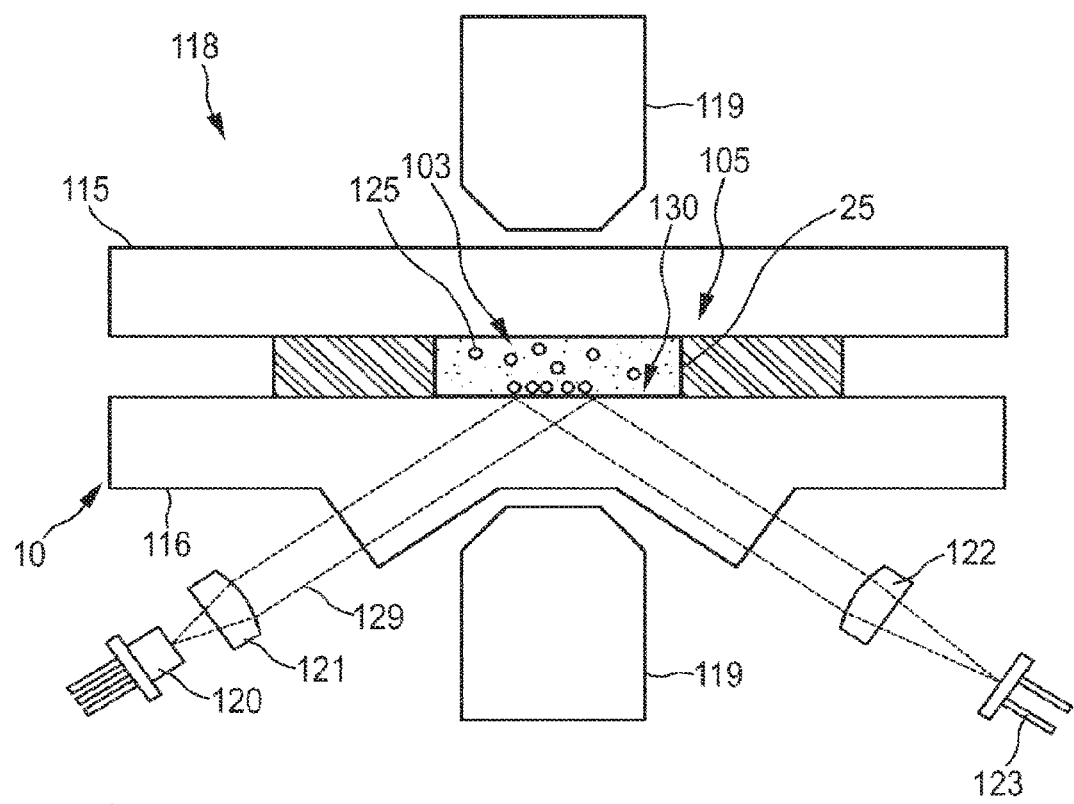
FIG. 15 shows schematically and exemplarily an embodiment of an analyzing apparatus.

FIG. 15 shows schematically and exemplarily a sensing part 118 of an analyzing apparatus for sensing a fluid, in which a sensing cartridge has been inserted. The analyzing apparatus serves to receive sensing cartridges such that the fluid can be examined in the measurement chamber. The sensing part 118 of the analyzing apparatus is adapted for determining a property of the fluid 103, which is located in the measurement chamber 25 of the sensing cartridge 10. The sensing part 118 of the analyzing apparatus comprises, in this embodiment, a magnetic element 119, which provides a magnetic field for forcing magnetic particles 125 within the measurement chamber 25 onto a surface 130 of the sensing cartridge 110. The magnetic particles 125 on the surface 130 are detected by, in this embodiment, illuminating this surface with a light beam 129 generated by a light source 120, which is, for example, a laser device or a LED, and by detecting the light reflected from the surface by a detector 123. The detector 123 is, for example, a photo detector or a two-dimensional camera. Optical elements 121 and 122 can be arranged in the light beam 129 for generating parallel light or focusing the light beam 129, respectively. The optical elements 121, 122 are preferentially lenses.

The configuration sketched in FIG. 15 shows a detection of changes at a surface using the FTIR method (frustrated total internal reflection). If a beam of light reflects on the interface between a medium with a higher refractive index, for example the measurement chamber 25, and a lower refractive index, for example the fluid, there is a certain critical angle of incidence above which there is a situation of total internal reflection (TIR). The present detection configuration (regarding refractive indices and angle of incidence) is such that there is total internal reflection of the incoming beam. Although the light is totally reflected in such a situation, there is still penetration of the light in a very thin layer of the medium with the low refractive index. This is called evanescent light, the intensity of which decays exponentially in the low refractive index medium with a characteristic penetration depth of the order of the wavelength of the light. So, in practice the penetration depth is preferentially less than 0.5 micrometer. If magnetic particles stick to the surface, the optical properties of this very thin first fluid layer of preferentially about 0.5 micrometer are changed leading to a reduction of the reflected light beam. This is caused by absorption and scattering of the evanescent light (FTIR; frustrated total internal reflection). As a result the signal of the photodetector changes.

Figure 16:
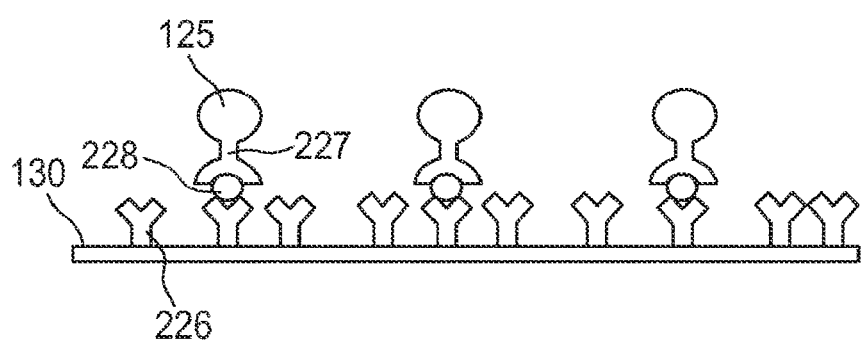
FIG. 16 shows schematically and exemplarily magnetic particles attached to a surface of a sensing device.

The objective is preferentially to detect specific target molecules or larger objects in the fluid. In the example sketched in FIG. 16 this is realized by a so-called sandwich assay. Magnetic beads 125 are coated with a specific antibody 227 that attaches to a target molecule 228 present in the fluid. When the magnetic beads 125 that are freely present in the fluid have reacted with the available target molecules the beads are attracted to the cartridge surface 130 that has been coated with another antibody 226 that can couple to the target molecule. After a sufficiently long reaction time the magnetic field is switched such that the magnetic beads are pulled upwards so that only the specifically bound beads with the correct target molecules stay attached to the surface. At that moment the optical detector can be read out and gives a signal that carries the information on the amount of target molecules in the fluid. So the detection location, in particular the surface 130, in particular a detection spot in the cartridge, is preferentially covered with a biolayer with antibodies.

The determination method described above with reference to FIGS. 15 and 16 is preferentially used by all embodiments of the sensing cartridge and the analyzing apparatus, which are described above. Correspondingly, the above described embodiments of the sensing cartridge and the analyzing apparatus are preferentially adapted such that they can perform the determination method described with reference to FIGS. 15 and 16. In particular, they comprise the features described with reference to FIGS. 15 and 16.

The features described above with respect to a sensing cartridge and/or an analyzing apparatus can also be embodied in other sensing devices for sensing a fluid that comprise a first end having at least one inlet port for receiving the fluid, a second end having at least one measurement chamber, at least one fluid channel coupling the at least one inlet port and the at least one measurement chamber for transporting fluid from the inlet port to the measurement chamber, and at least one fluid stop unit for stopping and controllably releasing the flow of fluid between the inlet port and the measurement chamber.

The fluid stop unit can be a single unit being adapted for stopping and/or controllably releasing the flow of fluid between the inlet port and the measurement chamber. In another embodiment, the fluid stop unit can also be a combination of units being adapted for stopping and/or controllably releasing the flow of fluid between the inlet port and the measurement chamber. Furthermore, the fluid stop unit can be a unit that cooperates with another unit, which might be present at the same sensing device or at another device like an analyzing apparatus, for stopping and/or controllably releasing a flow of fluid between the inlet port and the measurement chamber.

In the above described embodiment, the fluid can be blood or any other fluid, in particular, any other body fluid, like saliva or urine. The preferred application for the sensing cartridge and for the analyzing apparatus is in the field of point-of-care diagnostics, in particular, based on a finger prick blood sample, like a cardiac marker detection application. But, the sensing cartridge can also be adapted for filtering and/or debubbling of other fluids, like saliva for Drugs Of Abuse.

In the above described embodiment, the analyzing apparatus uses evanescent field techniques for determining the amount of magnetic particles on the surface. In other embodiments, other techniques can be used for determining these particles. For example, magnetic methods, sonic detection, electrical detection and combinations therefore can be used. Furthermore, the analyzing apparatus can comprise any sensor based on the detection of the magnetic properties of the particle on or near to a sensor surface. The analyzing apparatus can be adapted for detecting molecular targets, which often determine the concentration and/or presence of larger moieties, for example, cells, viruses, fractions of cells or fractions of viruses, tissue extract etc. The magnetic particles can be detected directly by the sensing method. As well, the particles can be further processed prior to detection, an example of further processing is that materials are added or that the chemical of biochemical of physical properties of the magnetic labels are modified to facilitate detection. The analyzing apparatus can be adapted for working together with several biochemical assay types, for example, binding/unbinding assay, sandwich assay, competition assay, displacement assay, enzymatic assay etc. The sensing cartridge and the analyzing apparatus can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The sensing cartridge and the analyzing apparatus can be used as rapid, robust and easy to use point-of-care biosensors for small sample volumes. The measurement chamber is preferentially a part of a disposable cartridge, which is to be used with the analyzing apparatus, which contains one or more magnetic field generating means, i.e. the magnetic element, and one or more detection means. The sensing cartridge and the analyzing apparatus can preferentially be adapted for a use in automated high-throughput testing.

The magnetic particles are preferentially nano-particles having at least one dimension ranging between 3 nm and 5000 nm, preferably between 10 nm and 3000 nm, more preferred between 50 nm and 1000 nm.

Other variations to the disclosed embodiment can be understood and effected by those skilled in the art in practising the claimed invention, from a study of the drawings, the disclosure and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. Analyzing apparatus for analyzing a fluid comprising:
   a sensing device including
      an inlet port for receiving the fluid,
      a measurement chamber for sensing the fluid,
      a fluid channel coupling the inlet port and the measurement chamber for transporting fluid from the inlet port to the measurement chamber, and
      a fluid stop unit for stopping and controllably releasing the flow of fluid between the inlet port and the measurement chamber, the fluid stop unit including
      a fluidic stop element configured to stop the flow of fluid between the inlet port and the measurement chamber;
   a venting hole arranged behind the measurement chamber with respect to a flow direction from the inlet port to the measurement chamber and coupled to the fluid channel, and
   a pressure control unit configured to selectively increase a pressure in a first part of the fluid channel between the inlet port and the fluidic stop element to force the fluid past the fluidic stop element, the pressure control unit being arranged at a first section of the device and being slidable between an open position and a closed position, wherein in the opened position the inlet port is uncovered by the pressure control unit and a first pressure is present in the first part of the fluid channel, wherein in the closed position the inlet port is sealed by the pressure control unit and a second pressure is produced in the first part of the fluid channel, and wherein the second pressure is higher than the first pressure to force the fluid in the fluid channel past the fluidic stop element into the at least one measurement chamber;

a sensing device receiving unit for receiving the sensing device; and fluid releasing unit for controllably releasing a flow of fluid stopped between the inlet port and the measurement chamber of the sensing device, when the sensing device is inserted into the sensing device receiving unit.

2. The analyzing apparatus according to claim 1, wherein the fluid releasing unit comprises:

a puncture element for puncturing a seal covering said venting hole when the sensing device is inserted into the sensing device receiving unit.

3. The analyzing apparatus according to claim 1, wherein the fluid releasing unit comprises a pressure generating unit; and a second hole coupled to the pressure generating unit for pressing a pressure fluid into a first hole or the inlet port of the sensing device when inserted into the sensing device receiving unit for increasing the pressure in the fluid channel such that the flow of fluid between the inlet port and the measurement chamber is controllably released.

4. The analyzing apparatus according to claim 1, wherein the fluid releasing unit comprises An actuator unit for pressing against an elastic cover of a sensing device inserted into the sensing device receiving unit for increasing the pressure in the fluid channel such that the flow of fluid between the inlet port and the measurement chamber is controllably released.

5. Method for sensing a fluid, comprising the acts of:

providing a sensing device comprising:

an inlet port for receiving the fluid;

a measurement chamber for sensing the fluid;

a fluid channel coupling the inlet port and the measurement chamber for transporting fluid from the inlet port to the measurement chamber; and a fluid stop unit for stopping and controllably releasing the flow of fluid between the inlet port and the measurement chamber, the fluid stop unit including a fluid stop element configured to stop the flow of fluid between the inlet port and the measurement chamber, a venting hole arranged behind the measurement chamber with respect to a flow direction from the inlet port to the measurement chamber and coupled to the fluid channel, and a pressure control unit configured to selectively increase a pressure in a first part of the fluid channel between the inlet port and the fluidic stop element to force the fluid past the fluidic stop element, the pressure control unit being arranged at a first section of the device and being slidable between an open position and a closed position, wherein in the opened position the inlet port is uncovered by the pressure control unit and a first pressure is present in the first part of the fluid channel, wherein in the closed position the inlet port is sealed by the pressure control unit and a second pressure is produced in the first part of the fluid channel, and wherein the second pressure is higher than the first pressure to force the fluid in the fluid channel past the fluidic stop element into the at least one measurement chamber;

receiving the fluid at the inlet port;

transporting the fluid from the inlet port to the measurement chamber by selective control of the pressure control unit to sense the fluid.

* * * * *